(12) United States Patent
Walen

(10) Patent No.: US 11,363,944 B2
(45) Date of Patent: Jun. 21, 2022

(54) SURGICAL INSTRUMENT WITH STEERABLE CAMERA

(71) Applicant: Stryker Corporation, Kalamazoo, MI (US)

(72) Inventor: James G. Walen, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 839 days.

(21) Appl. No.: 16/071,257

(22) PCT Filed: Feb. 10, 2017

(86) PCT No.: PCT/US2017/017409
§ 371 (c)(1),
(2) Date: Jul. 19, 2018

(87) PCT Pub. No.: WO2017/139604
PCT Pub. Date: Aug. 17, 2017

(65) Prior Publication Data
US 2021/0068647 A1 Mar. 11, 2021

Related U.S. Application Data

(60) Provisional application No. 62/444,005, filed on Jan. 9, 2017, provisional application No. 62/294,738, filed on Feb. 12, 2016.

(51) Int. Cl.
*A61B 1/233* (2006.01)
*A61B 1/005* (2006.01)
(Continued)

(52) U.S. Cl.
CPC .............. *A61B 1/233* (2013.01); *A61B 1/008* (2013.01); *A61B 1/0051* (2013.01);
(Continued)

(58) Field of Classification Search
CPC ............ A61B 1/233; A61B 1/06; A61B 1/015; A61B 1/12; A61B 1/0051; A61B 1/008;
(Continued)

(56) References Cited

U.S. PATENT DOCUMENTS 4,911,148 A * 3/1990 Sosnowski ........... A61B 1/0051
600/136
5,159,446 A * 10/1992 Hibino ............... A61B 1/00039
348/65
(Continued)

FOREIGN PATENT DOCUMENTS

WO WO-2008043100 A2 * 4/2008 ........... A61B 1/3132
WO 2016138443 A2 9/2016

OTHER PUBLICATIONS

International Search Report for Application No. PCT/US2017/017409 dated Aug. 1, 2017, 4 pages.

*Primary Examiner* — Aaron B Fairchild
*Assistant Examiner* — Shankar Raj Ghimire
(74) *Attorney, Agent, or Firm* — Howard & Howard Attorneys PLLC

(57) ABSTRACT

A surgical instrument for use on a patient. A tube assembly comprises an outer tube having a curved region, an inner tube disposed within the outer tube and comprising a single lumen, and a handle coupled to the outer tube. A viewing assembly is disposed within the single lumen. An actuation assembly is coupled to the inner tube and configured to steer the viewing assembly. The handle and the actuation assembly are complimentarily arranged such that the outer tube is positionable and the viewing assembly is steerable a user grasping the tube assembly with a single hand. The single lumen may define an irrigation flow path in communication with a fluid source and provide pressurized irrigation flow. An interior tube may be provided comprising an articulating region configured to articulate between a substantially (Continued)

curved condition and a substantially straight condition. Methods of manipulating an instrument are also disclosed.

14 Claims, 8 Drawing Sheets

(51) Int. Cl.
*A61B 1/008* (2006.01)
*A61B 1/015* (2006.01)
*A61B 1/06* (2006.01)
*A61B 1/12* (2006.01)

(52) U.S. Cl.
CPC ............ *A61B 1/0052* (2013.01); *A61B 1/015* (2013.01); *A61B 1/06* (2013.01); *A61B 1/12* (2013.01)

(58) Field of Classification Search
CPC .... A61B 1/0052; A61B 1/012; A61B 1/00066
See application file for complete search history.

(56) References Cited

U.S. PATENT DOCUMENTS

| | | | |
|---|---|---|---|
| 5,199,417 A * | 4/1993 | Muller | A61B 1/07 600/128 |
| 5,536,234 A | 7/1996 | Newman | |
| 5,549,547 A * | 8/1996 | Cohen | A61B 17/3203 604/30 |
| 5,733,242 A * | 3/1998 | Rayburn | A61B 1/0052 600/120 |
| 6,432,042 B1 * | 8/2002 | Bashour | A61B 1/00154 600/120 |
| 6,447,446 B1 | 9/2002 | Smith et al. | |
| 6,899,672 B2 * | 5/2005 | Chin | A61B 1/00071 600/121 |
| 7,479,106 B2 | 1/2009 | Banik et al. | |
| 8,323,241 B2 | 12/2012 | Salahieh et al. | |
| 8,419,623 B2 * | 4/2013 | Garcia | A61B 1/00105 600/136 |
| 8,449,520 B2 | 5/2013 | Pepper et al. | |
| 8,449,530 B2 | 5/2013 | Bacher et al. | |
| 8,690,764 B2 | 4/2014 | Clark et al. | |
| 8,708,953 B2 | 4/2014 | Salahieh et al. | |
| 8,920,369 B2 | 12/2014 | Salahieh et al. | |
| 9,101,735 B2 | 8/2015 | Rothe et al. | |
| 9,586,025 B2 | 3/2017 | Salahieh et al. | |
| 9,980,786 B2 | 5/2018 | Saul et al. | |
| 2006/0252993 A1 * | 11/2006 | Freed | A61M 25/0147 600/146 |
| 2009/0171159 A1 * | 7/2009 | Jorgensen | A61B 1/0055 600/139 |
| 2010/0256446 A1 * | 10/2010 | Raju | A61B 1/018 600/114 |
| 2010/0298642 A1 | 11/2010 | Trusty et al. | |
| 2010/0312056 A1 * | 12/2010 | Galperin | A61B 1/0051 600/141 |
| 2012/0197084 A1 * | 8/2012 | Drach | A61B 1/0008 600/123 |
| 2013/0102846 A1 | 4/2013 | Sjostrom et al. | |
| 2013/0190561 A1 | 7/2013 | Oskin et al. | |
| 2014/0018626 A1 | 1/2014 | Lee | |
| 2015/0038785 A1 | 2/2015 | Govrin et al. | |

* cited by examiner

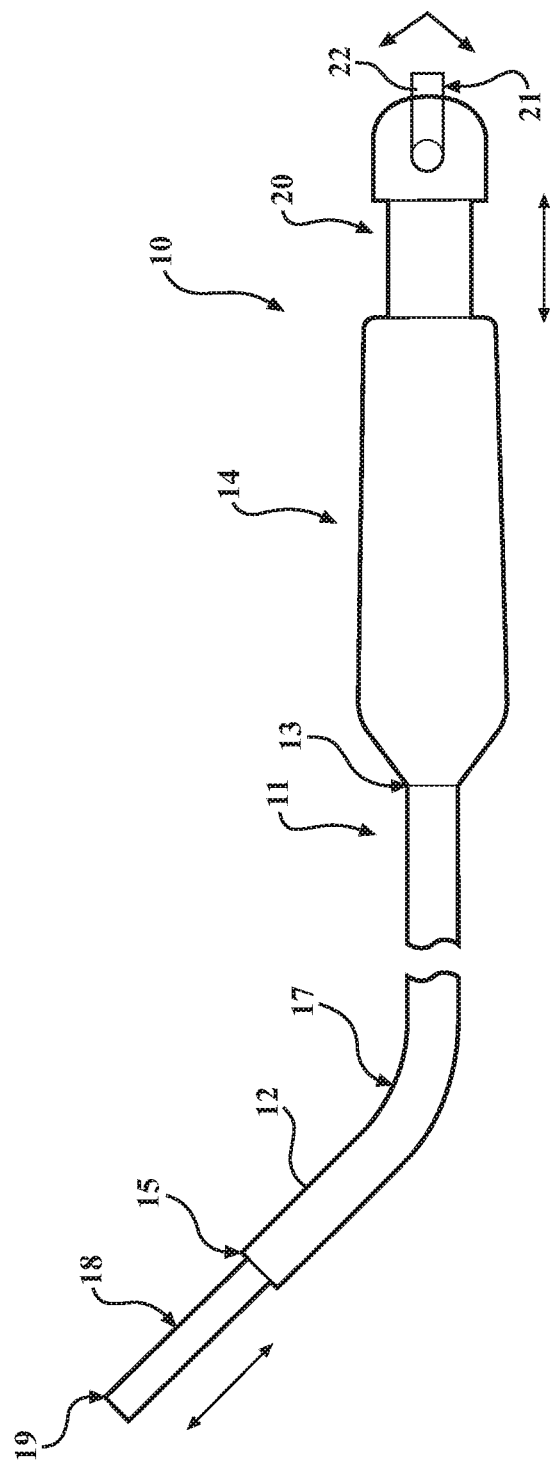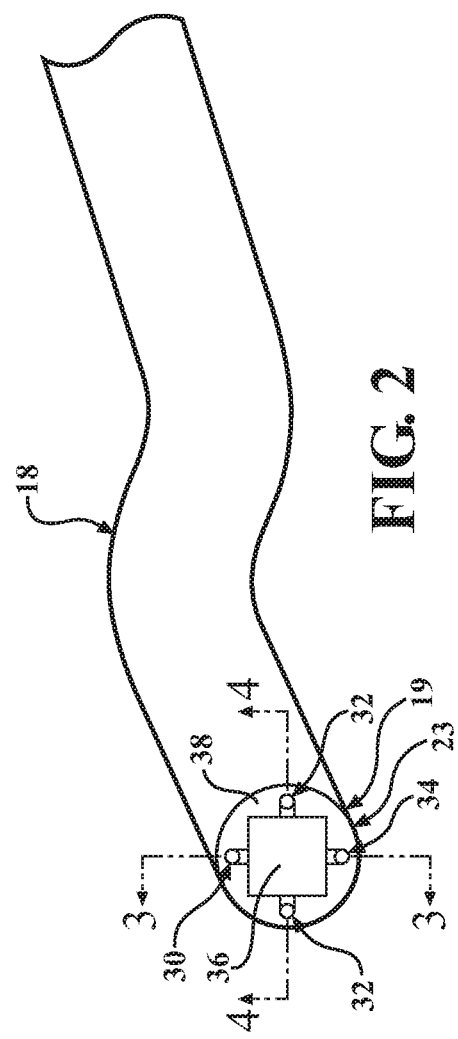
FIG. 1
FIG. 2

SURGICAL INSTRUMENT WITH STEERABLE CAMERA

CROSS-REFERENCE TO RELATED APPLICATIONS

The subject patent application is a U.S. National Stage of International Patent Application No. PCT/US2017/017409, filed on Feb. 10, 2017, which claims priority to and all the benefits of U.S. Provisional Patent Application No. 62/294,738, filed on Feb. 12, 2016, and U.S. Provisional Patent Application No. 62/444,005, filed on Jan. 9, 2017, the entire contents of each of which are hereby incorporated by reference.

TECHNICAL FIELD

The present invention relates generally to surgical instruments and, more particularly to, a surgical instrument with a steerable camera.

BACKGROUND

It is known that medical practitioners have found it useful to use surgical instruments to assist in the performance of surgical procedures. A surgical instrument is designed to be applied to a surgical site on the patient. The practitioner is able to position the surgical instrument at the site on the patient to perform a medical or surgical procedure. Today many procedures such lateral or central foraminal decompression must be performed by removing considerable healthy tissue, specifically the lamina and the facet joints, in order to access the portion of the foramen that is impinging neural elements. The added morbidity of resecting healthy tissue is due to surgeons lacking adequate tools to visualize or remove the impingement any other way.

Many devices have been developed for use in surgical procedures. They are valuable because they facilitate reduced incision size, improved access and visibility, while enhancing surgical outcome and quicker recovery. In many situations, as the surgical instrument is introduced to the surgical site, a distal end of the instrument, and tissue it contacts, is not visible to the surgeon because the instrument itself obstructs the surgeon's view. Curved instruments provide limited improvement for viewing a surgical field. However, with the surgeon's line of sight is limited to a straight line, the safety and effectiveness of these tools remains limited.

Many endoscopic surgical procedures require the use of a flexible or steerable endoscope to enable visualization of anatomy otherwise not visible with a rigid endoscope. One such device is a nasolaryngoscope. While highly effective for some needs such as visualizing the larynx of a patient, this device is not effective in many remote sinus areas.

While the traditional or open endoscopic techniques used today by surgeons provide a "global view" of the surgical site, there is a need to provide a secondary "local view" that is otherwise not available to the surgeon.

BRIEF DESCRIPTION OF THE DRAWINGS

FIG. 1 is an elevational view of a surgical instrument according to an exemplary embodiment of the present disclosure with the surgical instrument comprising a tube assembly having an outer tube and an inner tube disposed within the outer tube.

FIG. 2 is perspective view of a distal end portion of the inner tube of FIG. 1.

DETAILED DESCRIPTION

Figure 16:
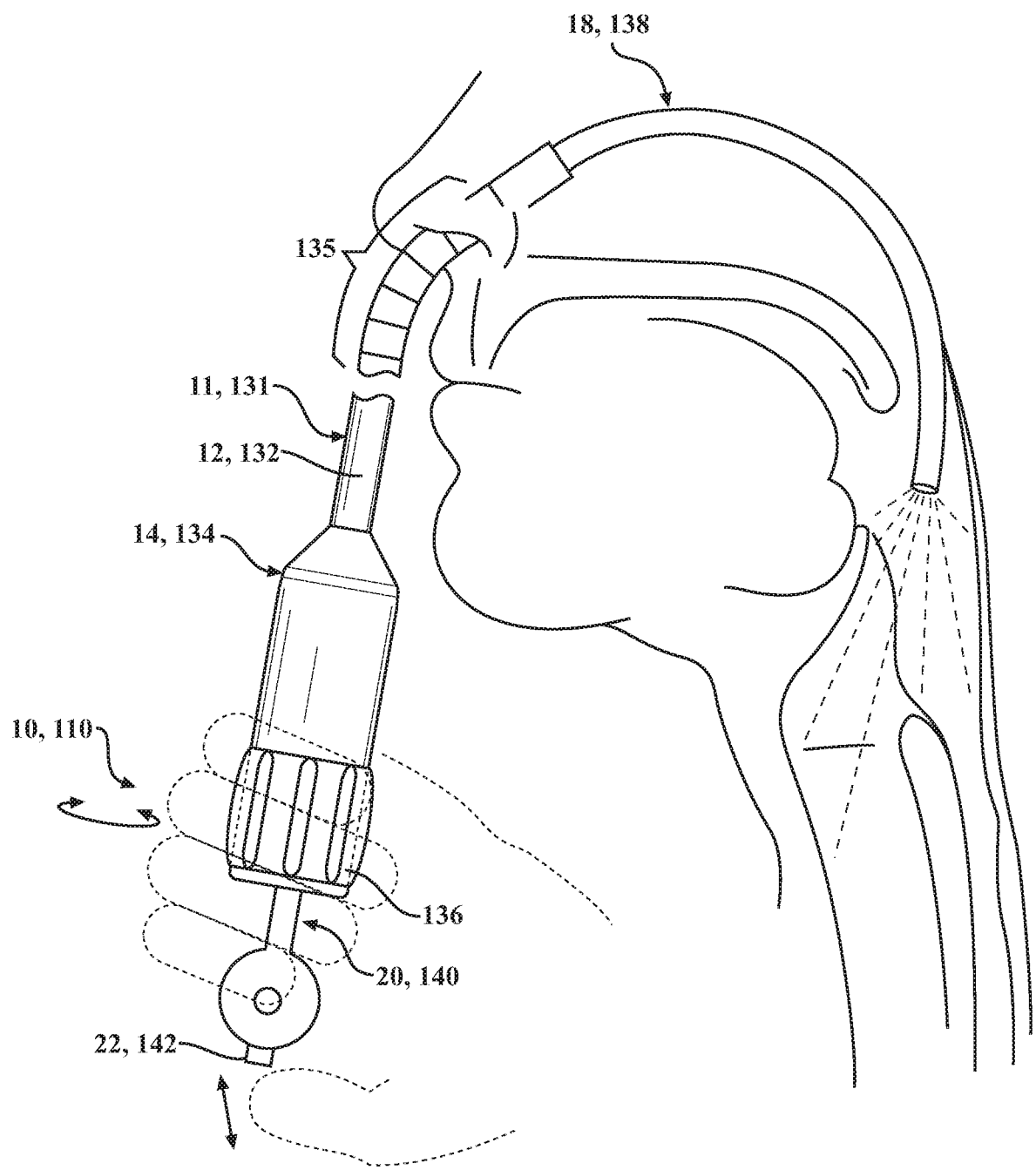
FIG. 16 is a diagrammatic view of the surgical instrument of FIG. 6 in use on a patient.

Referring to FIGS. 1 and 2, a surgical instrument 10 according to one embodiment of the present invention is shown for use on a patient, such as during a medical procedure (see FIG. 16). The surgical instrument 10 comprises a tube assembly 11. In one embodiment, the tube assembly 11 comprises an outer tube 12 having a proximal end 13 and a distal end 15 opposite the proximal end 13. A lumen extends between the proximal and distal ends 13, 15 of the outer tube 12.

The outer tube 12 comprises a curved region 17. The curved region 17 is intermediate the proximal and distal ends 13, 15 of the outer tube 12. In one embodiment, the curved region 17 of the outer tube 12 comprises a malleable material, such as thin walled aluminum, to allow at least a portion the outer tube 12 to be bent into shape to form the curved region 17 by a user's hands. In another embodiment, the curved region 17 of the outer tube 12 comprises a non-malleable material such that the curved region 17 is rigid (e.g., preformed during manufacturing). Exemplary materials include metals such as stainless steel or aluminum, or non-metallic materials such as a polymers or composites, and combinations thereof. It is contemplated that the entire outer tube may comprise the malleable material or the non-malleable material in certain embodiments. In still another embodiment to be described, the outer tube 12 is part of an articulating tube assembly as disclosed in International Patent Application No. PCT/US2016/019880, filed Feb. 26, 2016, the entire disclosure of which is hereby incorporated by reference.

The tube assembly 11 may further comprise an inner tube 18 disposed coaxially within the lumen of the outer tube 12. The inner tube 18 comprises a proximal end and a distal end 19 opposite the proximal end. In one embodiment, the inner tube 18 has an axial length longer than an axial length of the outer tube 12 such that the inner tube 18 extends past the distal end 15 of the outer tube 12 and/or the proximal end of the outer tube 12 when the inner tube 18 is disposed within the outer tube 12. A single lumen 25 extends between the proximal end and the distal end 19 of the inner tube 18, but plural lumens are contemplated in certain embodiments. The lumen of the outer tube 12 and the single lumen 25 of the inner tube 18 are preferably circular in cross section, but other suitable shapes are contemplated such as squares and higher order polygons.

At least a portion of the inner tube 18 is flexible, enabling it to flex, deform, and/or conform to the curved region 17 of the outer tube 12. The inner tube 18 may comprise a non-metallic material such as extruded polymer, braided assembly, or composite depending on the application. In embodiments with the outer tube 12 comprising malleable material, the inner tube 18 conforms to the curvature the user might impart to the outer tube 12 to form the curved region 17. In embodiments using the articulating tube assembly to be described, the inner tube 18 conforms to the curvature imposed by the articulation of the articulating tube assembly comprising the curved region 17 of the outer tube 12.

The outer tube 12 has a diameter greater than a diameter of the inner tube 18 such that the inner tube 18 may be disposed within the outer tube 12. In certain embodiments, the diameters of the inner tube 18 and outer tube 12 may be relatively small, such as approximately 1.0-3.0 millimeters (mm), so as to require only a small opening within the patient to, for example, extend into the nasal and sinus cavities. The wall thickness of the inner tube 18 and outer tube 12 may be relatively thin such as approximately 0.1-0.5 mm to allow the tube assembly 11 to be lightweight. It should be appreciated that the inner tube 18 and outer tube 12 may be scaled larger or smaller depending on the application.

The tube assembly 11 comprises a handle 14 coupled to the outer tube 12. The handle 14 is coupled to the proximal end 13 of the outer tube 12 through joining means commonly known in the art. The handle 14 and the outer tube 12 may be of unitary construction. The handle 14 is configured to be grasped by the user for functions to be described. The handle 14 may assume any suitable shape or configuration. In one embodiment, the handle 14 is configured to be grasped by a user's palm.

The surgical instrument 10 comprises an actuation assembly 21 coupled to the inner tube 18. The actuation assembly 21 is configured to steer the inner tube 18 from a location at or proximate the distal end 19. FIG. 1 shows an exemplary embodiment of the actuation assembly 21 comprising a movable lever 22. In some embodiments, the lever 22 is a joystick capable of articulating the distal end 19 of the inner tube 18 within, for example, a single plane. Other embodiments of the actuation assembly 21 are contemplated to cause steering of the distal end 19 of the inner tube 18, along multiple planes or single planes, depending on the desired functionality.

It should be appreciated that the actuation assembly 21 is configured to provide steering when the distal end 19 of the inner tube 18 is protruding from the outer tube 12. For example, when the distal end 19 of the inner tube 18 is protruding from the distal end 15 of the outer tube 12, actuating the lever 22 of the actuation assembly 21 causes the exposed portion of the distal end 19 of the inner tube 18 to deflect. In certain embodiments, when the distal end 19 of the inner tube 18 is proximal the distal end 15 of the outer tube 12 (i.e. within the outer tube 12), actuating the lever 22 does not cause the inner tube 18 to deflect because the inner tube 18 is constrained by the outer tube 12. The greater the protruding of the inner tube 18 from the outer tube 12 may provide selective control of the radius of curvature of the inner tube 18 upon actuation of the actuation assembly 21. In other words, actuating the actuation assembly 21 results in a greater radius of curvature when the inner tube 18 is protruding more prominently from the outer tube 12. It should be appreciated that the outer tube 12 may be articulated regardless of how the inner tube 18 is positioned; e.g., the outer tube 12 comprising the malleable material may be bent by the user with the inner tube 18 positioned therein.

Figure 3:
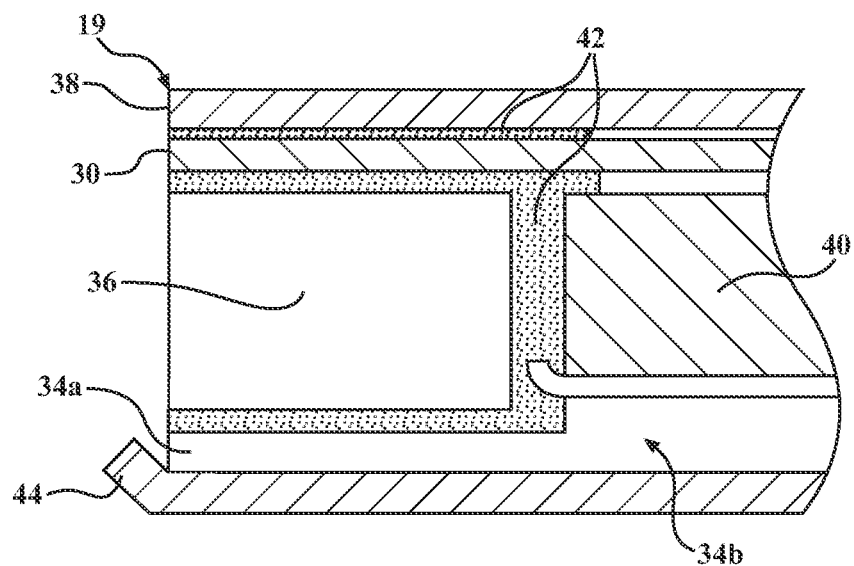
FIG. 3 is a sectional view taken along line 3-3 of FIG. 2.
Figure 4:
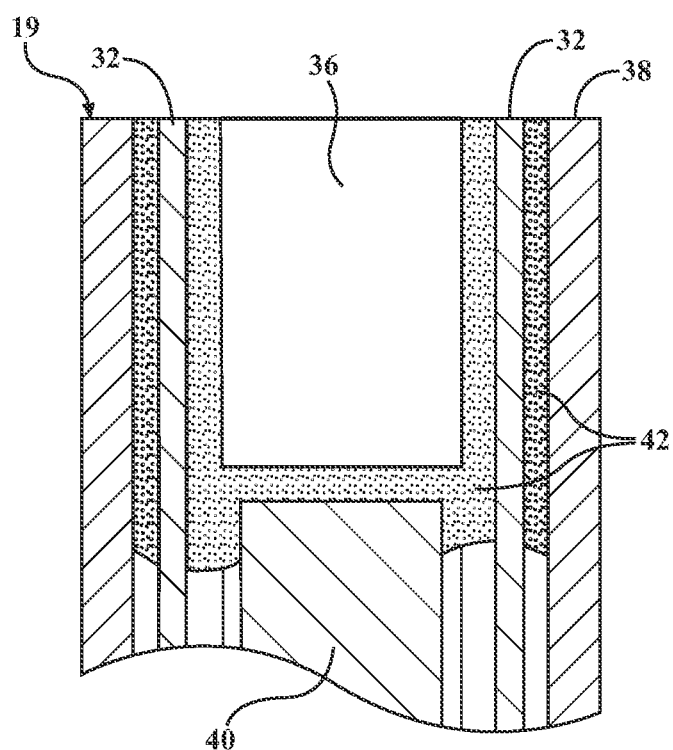
FIG. 4 is a sectional view taken along line 4-4 of FIG. 2.

Referring to FIGS. 2-4, the surgical instrument 10 further comprises a viewing assembly 23 disposed within the single lumen 25 and coupled to the inner tube 18. The viewing assembly 23 is positioned within a distal section or at the distal end 19 of the inner tube 18. The viewing assembly 23 is configured to visualize within a cavity or within the patient.

The actuation assembly 21 is configured to steer the viewing assembly 23 when the distal end 19 of the inner tube 18 is protruding from the distal end of the outer tube 12. Referring to FIGS. 1 and 16, the handle 14 and the actuation assembly 21 may be complimentarily arranged such that the outer tube 12 is positionable within the patient with the handle 14 and the viewing assembly 23 is steerable with the actuation assembly 21 by the user grasping the tube assembly 11 with a single hand. In other words, a single hand may both position the outer tube 12 and steer the viewing assembly 23 by virtue of control of the inner tube 18, simultaneously. In one example, the user may position the outer tube 12 within the orifice, and subsequently, with the same hand, steer the viewing assembly 23 coupled to the inner tube 18. It is understood that the hand comprises a palm and a thumb. In a possible embodiment, the tube assembly 11, such as the handle 14, is adapted to be grasped with the palm of the hand and the actuation assembly 21 adapted to be controlled with the thumb of the hand. This allows the user to use the second hand to control or otherwise manipulate a second surgical tool allowing enhanced control at the surgical site.

Referring to FIG. 1, the tube assembly 11 may comprise a second handle 20 coupled to the inner tube 18. The second handle 20 may be positioned proximal to the handle 14 coupled to the outer tube 12. A proximal portion of the handle 20 of the inner tube 18 protrudes or extends from the handle 14 of the outer tube 12. The actuation assembly 21 may be coupled to the second handle 20. The handles 14, 20 are complimentarily arranged such that the outer tube 12 is positionable within the patient and the viewing assembly 23 steerable within the patient with the actuation assembly 21 by the user grasping the handles 14, 20 with the single hand, such as grasping both handles 14, 20 with the palm and fingers of the single hand.

In certain embodiments, the handles 14, 20 are axially movable relative to one another. The relative movement of the handles 14, 20 provides the inner tube 18 moving axially relative to the outer tube 12 so as to control the protrusion of the distal end 19 of the inner tube 18 from the distal end 15 of the outer tube 12. In operation, the user may slide the inner tube 18 and its handle 20 axially with respect to the outer tube 12 and its handle 14, as indicated by the arrows, to a desired position such that the distal end 19 of the inner tube 18 is aligned with or protruding from the distal end 15 of the outer tube 12. In certain embodiments, the user may position the outer tube 12 adjacent to the orifice, and subsequently, with the same hand, control the protrusion the inner tube 18 from the outer tube 12 by axially moving the second handle 20 relative to the handle 14. Then, with the same hand, such as with the thumb, steer the viewing assembly 23 coupled to the inner tube 18 using the actuation assembly 21. The position of the outer tube 12 may be simultaneously adjusted with the same, single hand. It should be appreciated that such deployment of the inner tube 18 may be useful after the distal end 15 of the outer tube 12 is placed at a desired location of the patient, such as the surgical site.

Figure 14:
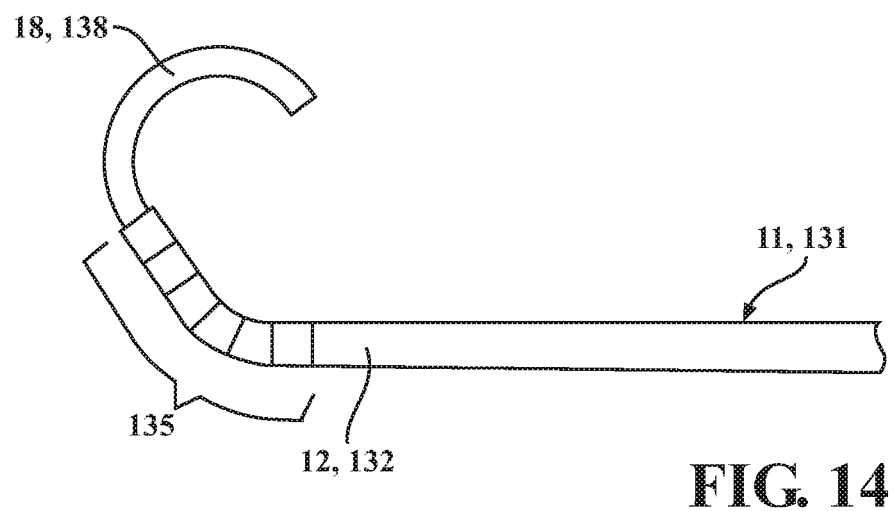
FIG. 14 is an elevational view of the surgical instrument of FIG. 6 in a second operational position.
Figure 15:
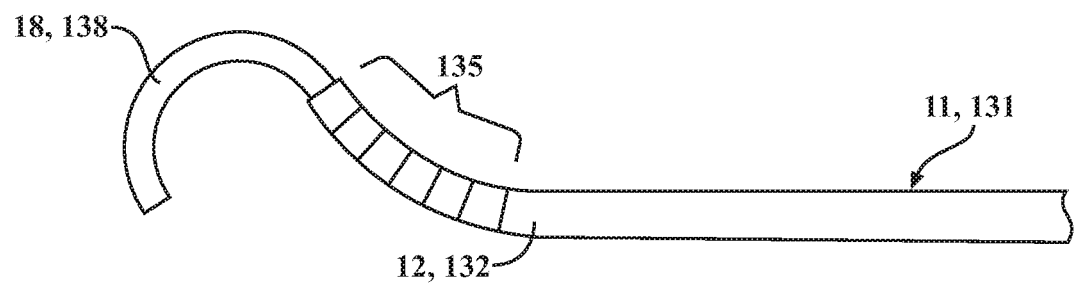
FIG. 15 is an elevational view of the surgical instrument of FIG. 6 in a third operational position.

The outer tube 12 and the inner tube 18 may curve on a single plane such that the curved region 17 of the outer tube 12 and the inner tube 18 curve in either the same direction or opposite directions (within the single plane). FIG. 14 shows the curved region 17 of the outer tube 12 and the inner tube 18 curving in the same direction. This type of compound articulation provides for, among other advantages, a greater radius of curvature for the tube assembly 11 than either the outer tube 12 or inner tube 18 alone. FIG. 15 shows the curved region 17 of the outer tube 12 and the inner tube 18 curving in opposite directions. This type of compound articulation provides for, among other advantages, the ability to access (e.g. view with the viewing assembly 23) the surface(s) of structures positioned opposite the orifice through which the tube assembly 11 was positioned. The present disclosure contemplates the inner tube 18 may not be constrained to a single plane such that the inner tube 18 protruding from the outer tube 12 may be steered in a second or third dimension relative to an axis of the tube assembly or relative to the axis of the distal end of the outer tube 12.

Referring to FIGS. 2-4, the inner tube 18 is formed from a shroud or an extrusion 38 with the single lumen 25 defined by the extrusion 38. The extrusion 38 may comprise a distal end defined by the distal end 19 of the inner tube 18, as shown in FIGS. 3 and 4. In certain embodiments, the extrusion 38 is the primary outer component of the inner tube 18 from the distal end towards the proximal end. The extrusion 38 may define a generally arcuate configuration to form a passageway for structures to be described. It should be appreciated that the extrusion 38 may be comprised of the same material as the inner tube 18, or a different metallic and/or non-metallic material(s) depending on the requirements of the application.

In certain embodiments, the actuation assembly 21 comprises a steering assembly with one or more steering control members 32 such as cables or stranded wire. The steering control members 32 are connected to the distal end of the extrusion 38 by the adhesive 42. A flex core 40 may be provided and coupled to the steering control members 32. The flex core 40 is flexible member configured to constrain the steering control members 32 to a longitudinal channel within the extrusion 38, as shown in FIGS. 3 and 4. Tensioning one steering control member 32 while releasing the other steering control member 32 causes the inner tube 18 to flex in the direction of the tensioned one of the steering control members 32. It should be appreciated that the flex core 40 may be solid, hollow, or a combination thereof.

The viewing assembly 23 may comprise an illumination assembly. In one embodiment, the illumination assembly comprises one or more illuminators or light fibers 30, such as light emitting diodes (LEDs), located at the distal end of the extrusion 38. The light fibers 30 may be located on one side of an image sensor 36 to be described. The light fiber 30 may be coupled to the distal end of the extrusion 38 or inner tube 18 by an adhesive 42 such as an epoxy or ultraviolet (UV) cure adhesive. The light fibers 30 are in communication to a light or power source (not shown). It should be appreciated that the light fibers 30 may be configured as a plastic optical fiber coupled to the light source disposed on or within at least one of the handles 14, 20. It should also be appreciated that, in another embodiment, the image sensor 36 may also be disposed on or within at least one of the handles 14, 20, and the remote light source and image sensor 36 may communicate wirelessly. In one embodiment, the steering control members 32 comprise light fibers so that the steering control members 32 also transmit light while providing the steering function. In such an embodiment, the light fibers 30 may be eliminated.

The tube assembly 11 may comprise an irrigation flow path 34. The single lumen 25 of the inner tube 18 may define the irrigation flow path 34 in communication with a fluid source (not shown). In certain embodiments, the irrigation flow path 34 is configured to irrigate the viewing assembly 23. The single lumen 25 may comprise a proximal region comprising the proximal end of the inner tube 18, and a distal region comprising the distal end 19 of the inner tube 18. The proximal region comprises a cross-sectional area greater than a cross-sectional area of the distal region to provide a nozzle-type effect for pressurized irrigation flow. Referring to FIG. 3, the irrigation flow path 34 may comprises a distal irrigation flow path 34a. The distal irrigation flow path 34a may be provided within the distal region of the inner tube 18. The irrigation flow path 34 may further comprise a proximal irrigation flow path 34b disposed provided within the proximal region of the inner tube 18 and between the distal irrigation flow path 34a and the proximal end of the inner tube 18. The proximal irrigation flow path 34b comprises a greater cross-sectional area than the distal irrigation flow path 34a. More specifically, the cross-sectional area of the distal irrigation flow path 34a is limited by the image sensor 36 and the light fiber 30, whereas the cross-sectional area of the proximal irrigation flow path 34b is limited by the light fiber 30, the steering control members 32, and the flex core 40. In certain embodiments, the cross-sectional area of the proximal irrigation flow path 34b is at least 50, 75, 100, 125, 150, 175, 200, 225, or 250%, larger than the distal irrigation flow path 34a. The reduction in cross-sectional area within the single lumen 25 as the proximal irrigation flow path 34b transitions to the distal irrigation flow path 34a provides for a corresponding increase in pressure generally in accordance with the ideal gas law. It should be appreciated that the irrigation flow path 34 is optional, and in other embodiments, the fluid source comprises an irrigation reservoir disposed in at least one of the handles 14, 20.

The surgical instrument 10, and more particularly the tube assembly 11, may comprise a deflector 44 coupled to the distal end 19 of the inner tube 18. The deflector 44 is configured to deflect the pressurized irrigation flow towards the viewing assembly 23 including the image sensor 36 and the light fibers 30, as shown in FIG. 3. The deflected irrigation flow improves visibility of the viewing assembly 23 by clearing away debris disposed on or immediately ahead of the image sensor 36.

Figure 5:
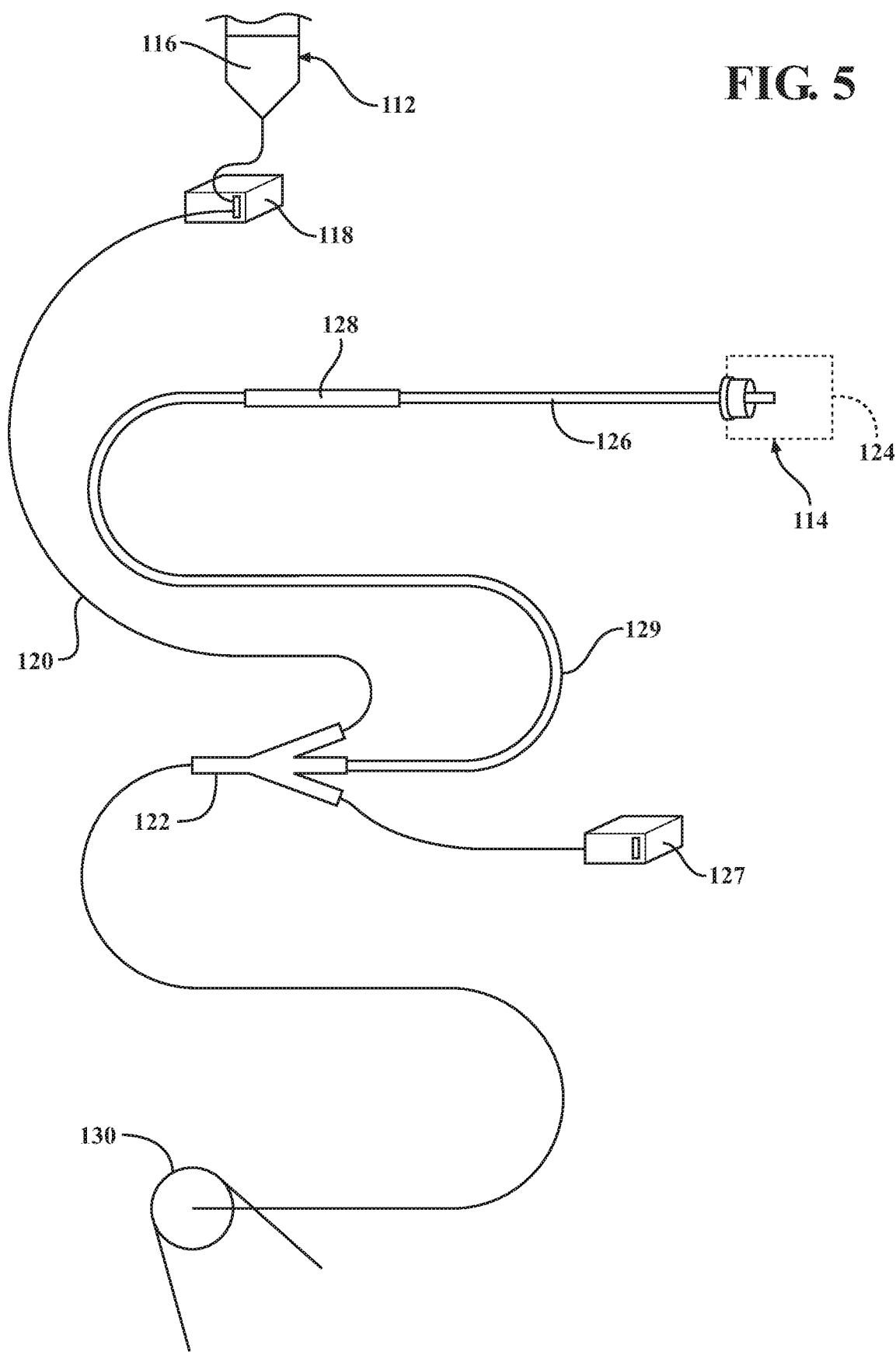
FIG. 5 is a schematic view of a surgical instrument according to an exemplary embodiment of the present disclosure in an operational relationship with an irrigation system and an illumination system.

The viewing assembly 23 comprises the image sensor 36 such as a camera, imaging element, video camera, or a camera chip, in communication with an image processing unit 127 (see FIG. 5). In operation, such as during a surgical procedure, the viewing assembly 23 provides real time video to be presented to the user on a video monitor (not shown) for a primary view. In certain embodiments, the viewing assembly 23 provides a picture-in-picture video on the video monitor as a secondary view for an endoscope (not shown).

In such an embodiment, the user maintains the "global view" with current visualization tools supplemented with perspective view deeper within the surgical site or cavity. The viewing assembly 23 coupled to the inner tube 18 may be advanced or retracted relative to the outer tube 12 during the surgical procedure from a retracted position in which the viewing assembly 23 is proximal of the distal end 15 of the outer tube 12, to an advanced position in which the viewing assembly 23 is barely protruding of the distal end 15 of the outer tube 12, to even more advanced positions in which the viewing assembly 23 is more prominently protruding of the distal end 15 of the outer tube 12.

In certain embodiments, the inner tube 18 may be configured to receive structures described herein, such as the imaging assembly, the illumination assembly, the irrigation assembly, and the like. In other embodiments, single lumen 25 of the inner tube 18 functions solely as a working channel capable of receiving any variety of working tools or devices such as graspers, cutter, power shavers, drills, radiofrequency devices, suction, etc. In still other embodiments, the surgical instrument 10 may provide one or more of these working tools as part of the inner tube 18.

FIG. 5 shows a schematic representation of another exemplary embodiment of a surgical instrument 110 for use on a patient, such as during a medical procedure. The surgical instrument 110 of FIG. 5 is illustrated in operational relationship with an irrigation system 112, an illumination system 114, and the image processing unit 127. The irrigation system 112 comprises a fluid source 116 (e.g., a reservoir of saline solution), a console 118 having a pump (not shown) for pumping the fluid from the fluid source 116, and a fluid conduit 120 for conveying the pumped fluid from the console 118 to a connector 122. The illumination system 114 comprises a light source 124 (e.g., an LED) and at least one light fiber 126 connected to the light source 124 for transmitting the light to another connector 128. Another conduit 129 interconnects the connectors 122, 128. The image processing unit 127 is in communication with the imaging sensor 144 of the surgical instrument 110 and configured to receive imaging signals, such as real time video, from the imaging sensor 144 to present to the user on a video monitor. The image processing unit 127 may be coupled to the connector 122. A distal end of the surgical instrument 110 is shown schematically at 130 with light emitted therefrom. It should be understood the operational relationship shown in FIG. 5 may alternatively comprise the surgical instrument 10 of the previous embodiment.

Figure 6:
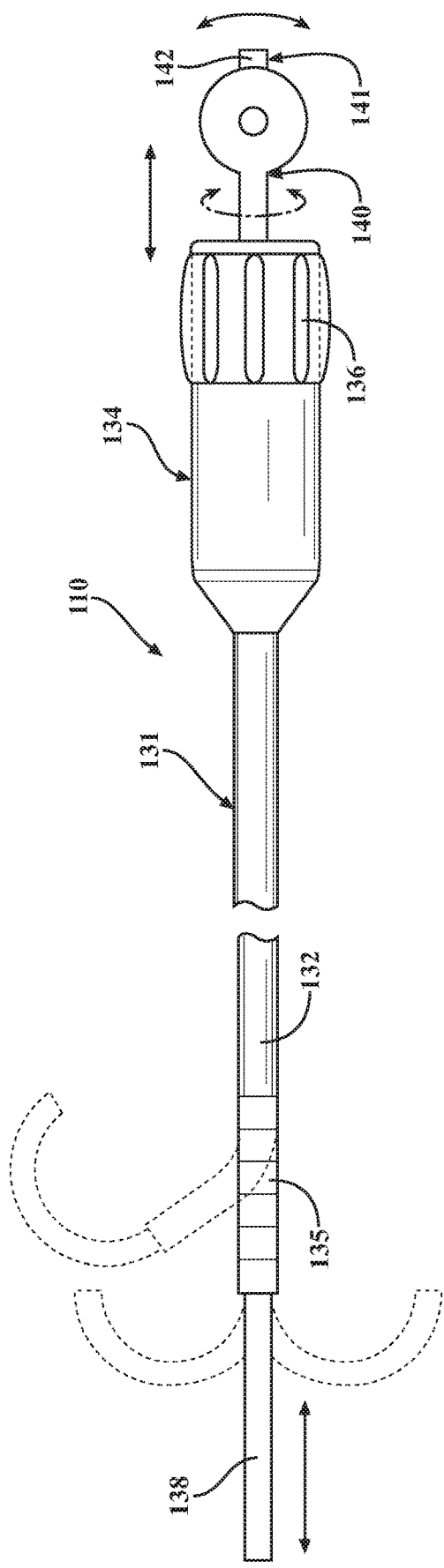
FIG. 6 is an elevational view of the surgical instrument of FIG. 5 with the surgical instrument comprising a tube assembly having an outer tube and an inner tube disposed within the outer tube.

Referring to FIG. 6, in another embodiment, the surgical instrument 110 comprises a tube assembly 131. The surgical instrument 110 and tube assembly 131 may include any of the features described above (i.e., the features described throughout this disclosure are interchangeable between the various embodiments). The tube assembly 131 comprises an outer tube 132 and an inner tube 138 disposed coaxially within the outer tube 132. The inner tube 138 forms a single lumen 139 (see FIG. 7). A handle 134 may be coupled to the outer tube 132, and a second handle 140 coupled to the inner tube 138. The second handle 140 may be axially movable and/or rotatable relative to the handle 134, as shown by the arrows, to position the inner tube 138 protruding from the outer tube 132 in at least one plane.

The surgical instrument 110 comprises an actuation assembly 141 for steering the inner tube 138 and a viewing assembly 143 to be described. In one embodiment, the actuation assembly 141 is a joystick 142 for steering the inner tube 138. In a preferred embodiment, the actuation assembly 141 is configured to impart a relative axial force between the outer tube 132 and an interior tube 137 fixedly coupled distal the articulating region 135 in a manner to be described. Referring to FIGS. 6 and 16, the handle 134 and the actuation assembly 141 are complimentarily arranged such that the outer tube 132 is positionable within the patient with the handle 134 and the viewing assembly 143 is steerable by the user grasping the tube assembly 121 with a single hand. The single hand may both position the outer tube 132 and steer the viewing assembly 143 coupled to the inner tube 138. In one example, the user may position the outer tube 132 within the orifice, and subsequently, with the same hand, steer the viewing assembly 143 coupled to the inner tube 138. The tube assembly 131 may be adapted to be grasped with a palm of the hand and the actuation assembly 21 adapted to be controlled with a thumb of the hand. In certain embodiments, the second handle 140 may be positioned proximal to the handle 134 coupled to the outer tube 132 with the actuation assembly 141 coupled to the second handle 140. The handles 134, 140 are complimentarily arranged such that the outer tube 12 is positionable within the patient and the viewing assembly 143 steerable within the patient with the actuation assembly 141 by the user grasping the handles 134, 140 with the single hand.

Referring to FIGS. 9-12, the surgical instrument 110, and more particularly the tube assembly 121, may comprise an interior tube 137 disposed within the lumen of the outer tube 132 and about the inner tube 138. The interior tube 137 comprises a distal end 147 and a proximal end opposite the distal end. An axis 145 may be defined between the distal end 147 and the proximal end. A lumen extends between the distal end 147 and the proximal end with the lumen configured to receive the inner tube 138.

Figure 13:
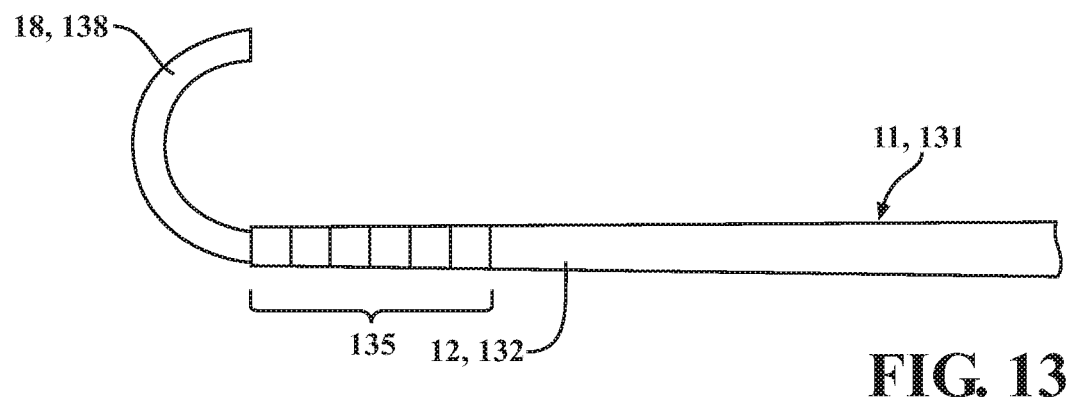
FIG. 13 is an elevational view of the surgical instrument of FIG. 6 in a first operational position.

The interior tube 137 further comprises the articulating region 135. The curved region 17 of the outer tube 12 further comprises the articulating region 135 (see FIGS. 13-15). In embodiments with the interior tube 137, the articulating region 135 of the outer tube 132 and the interior tube 137 (not the inner tube 138) articulate in manner to be described and further disclosed in International Patent Application No. PCT/US2016/019880, which is hereby incorporated by reference. The inner tube 138 comprising the viewing assembly, the illumination assembly, the irrigation assembly, and the like, may be advanced within the lumen of the interior tube 137 with articulating region 135 in a substantially curved condition relative to the axis 145, a substantially straight condition relative to the axis 145, or any condition therebetween. The surgical instrument 110 may comprise a rotatable collar 136 rotatably coupled to the handle 134 and configured to lock the articulating region 135 in the substantially curved condition and/or the substantially straight condition.

The interior tube 137 may be fixed to the outer tube 132 distal to the articulating region 135, and axially movable relative to the outer tube 132 proximal to the articulating region 135 in one of a first or second direction. The second direction may be opposite the first direction such that the interior tube 137 and outer tube 132 may be pushed and pulled relative to each other via, for example, the handles 134, 140.

Referring to FIGS. 9-12, the articulating region 135 of the interior tube 137 comprises apertures 166, beams 168, tie straps 170, apertures 172, and bottom segments 174. The apertures 166 extend through the interior tube 137 and may be formed through a cutting process such as laser cutting. In the illustrated embodiment, the apertures 166 are generally rectangular, but other suitable shapes are contemplated. The apertures 166 may have an axial length greater than a circumferential width. The plurality of beams 168 may be defined by the apertures 166 and 172. The beams 168 extend axially in a generally linear fashion. The beams 168 may parallel and/or radially positioned approximately ninety degrees (90°) from each other. It should be appreciated that each of the beams 168 may be one continuous axially extending beam or a plurality or series of axially extending beams 168. It should further be appreciated that the beams 168 are configured to bend and transfer forces under tension or compression.

The tie straps 170 may be defined by the apertures 166. The tie straps 170 extend circumferentially between and spaced axially along the beams 168. The tie straps 170 are configured to maintain a generally cylindrical profile of the articulating region 135 of the interior tube 137 and prevent the beams 168 from buckling during compression of the interior tube 137.

The apertures 172 extend radially through the interior tube 137 below the beams 168. The apertures 172 have an inverted generally pentagonal shape. The apertures 172 may be formed by cutting the interior tube 137. The bottoming segments 174 formed by cutting the apertures 172 disposed below and extending from the beams 168. The bottoming segments 174 are generally triangular or pentagonal in shape, but may be any suitable shape. The bottoming segments 174 extend circumferentially between and spaced axially along the beams 168. Each of the bottoming segments 174 have a lower side that is inclined by a predetermined angle, such as, for example, approximately two and one half degrees (2.5°). The bottoming segments 174 may comprise a bottom that extends axially a distance greater than a top thereof. An axial space or gap separates the bottoming segments 174 such that the bottoming segments 174 are configured to bottom out and provide surface to surface contact against each other in an articulated or curved configuration as to be described. In one embodiment, the curved condition comprises an angular displacement of three and one-half degrees (3.5°) or four degrees (4°), but other angular displacements such as 10°, 20°, or 30° or more are within the scope of the present disclosure.

The articulating region 135 of the outer tube 132 comprises apertures 176, beams 178, tie straps 180, apertures 182, and bottoming segments 184. The apertures 176 extend through the outer tube 132. In the illustrated embodiment, the apertures 176 are generally rectangular in shape. The apertures 176 are formed within the outer tube 132 through a cutting process such as laser cutting. The outer tube 132 comprises the beams 178 defined by the apertures 176. The beams 178 extend axially in a linear fashion. The beams 178 are parallel to each other and/or radially positioned approximately ninety degrees (90°) circumferentially from each other. It should be appreciated that the beams 168 are configured to bend and transfer forces under tension or compression. It should further be appreciated that each of the beams 178 may instead be one continuous axially extending beam or a plurality or series of axially extending beams 178.

The tie straps 180 may be defined by the apertures 176 extending circumferentially between and axially spaced along the beams 178. The tie straps 180 prevent the beams 178 from buckling during axial compression of the outer tube 132. The tie straps 180 are generally "V" shaped with the "V" opening proximally to prevent snagging on the bottoming segments 174 of the interior tube 137 when the tube assembly 131 is articulated. It should be appreciated that the tie straps 180 maintain a cylindrical profile of the articulating region 135 of the outer tube 132 and prevent the beams 178 from buckling during compression of the outer tube 132.

Figure 10:
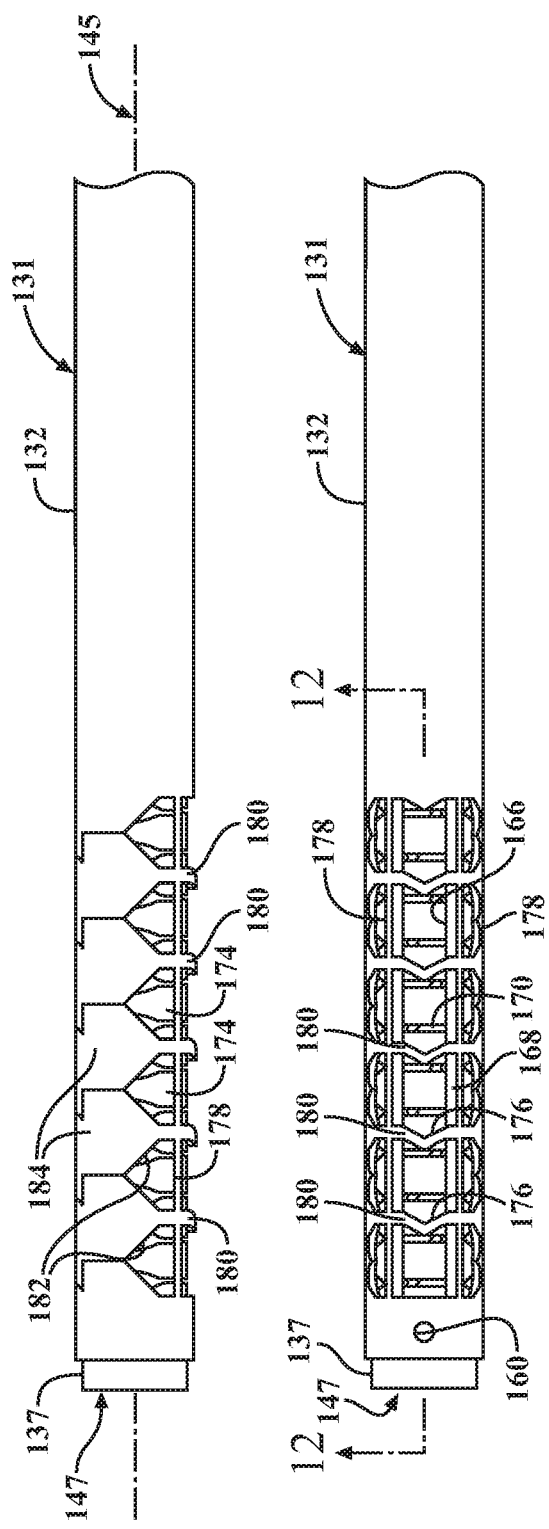
FIG. 10 is a side elevational view of the articulating region of FIG. 9.
Figure 11:
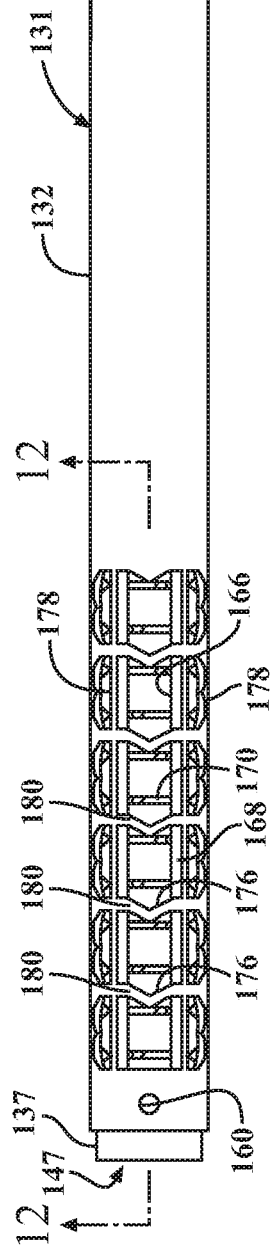
FIG. 11 is a top plan view of the articulating region of FIG. 9.
Figure 12:
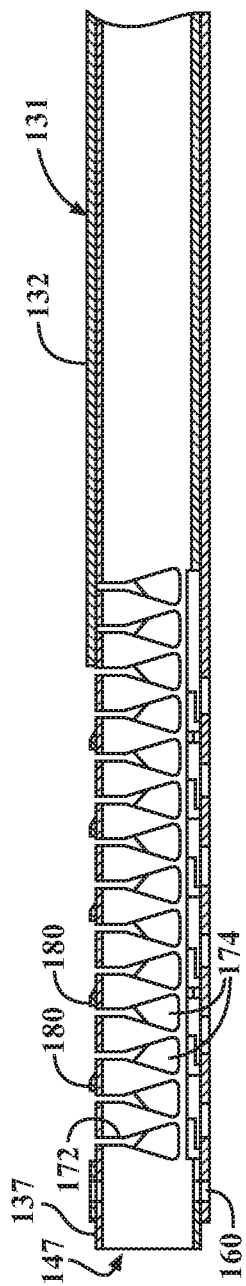
FIG. 12 is a sectional view taken along line 12-12 of FIG. 11.

The apertures 182 extend radially through the outer tube 132 below the beams 178. The apertures 182 may an inverted pentagonal shape as shown in FIG. 10. The apertures 182 are formed within the outer tube 132 through a cutting process such as laser cutting. The bottoming segments 184 may be further defined by the apertures 182 and positioned below the beams 178. The bottoming segments 184 may be generally pentagonal in shape. The bottoming segments 184 extend circumferentially between and are spaced axially along the beams 178. The bottoming segments 184 have a bottom that extends axially a distance greater than a top thereof. Other than being discrete structures separated by an interface, no axial gap or a negligible axial gap may be provided between adjacent bottoming segments 184 such that the bottoming segments 184 are configured to provide rigidity in a substantially straight configuration relative to the axis 145.

Figure 9:
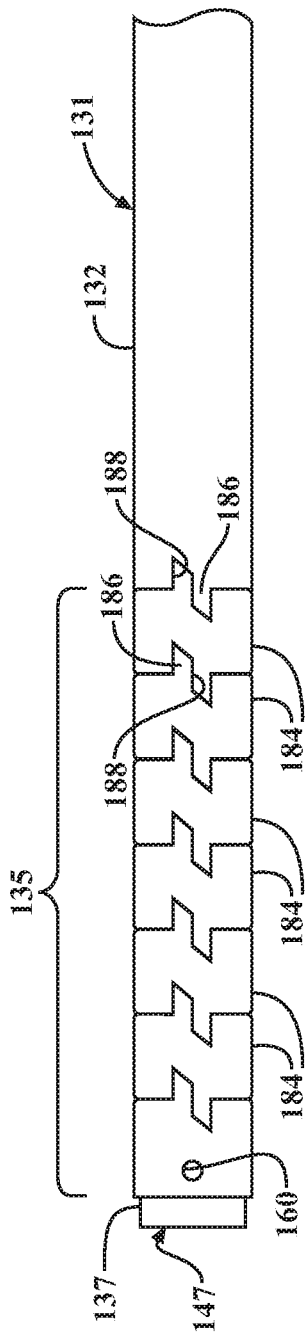
FIG. 9 is a bottom plan view of an articulating region of the tube assembly of the surgical instrument of FIG. 6 with an interior tube disposed within the outer tube.

Each bottom of the bottoming segments 184 may comprise a protrusion 186 and a recess 188 as shown in FIG. 9. The recess 188 of one of the bottoming segments 184 receives the protrusion 186 from an adjacent one of the bottoming segments 184. The interference between the protrusions 186 and the recesses 188 prevent relative rotation of adjacent bottom segments 184.

The interior tube 137 may comprise a greater number of apertures 172 defining the bottoming segments 174 than the outer tube 132. For example, the interior tube 137 has fourteen apertures 172 and thirteen bottoming segments 174, and the outer tube 132 has six apertures 182 and five bottoming segments 184. The relative number of bottoming segments 174, 184 between the interior tube 137 and the outer tube 132 may impart desired bending characteristics to the articulating region 135, such as the radius of curvature, at certain applied forces to be described. It should be appreciated that, in other embodiments, the number of apertures 172, 182 and bottoming segments 174, 184 may be greater or less.

In one operational example, the interior tube 137 is pushed distally with respect to the outer tube 132 to move the outer tube 132 proximally with respect to the interior tube 137. The beams 178 of the outer tube 132 are put in compression and the beams 168 of the interior tube 137 are put in tension. The counterposing loading causes a curve in the articulating region 135 of the tube assembly 131 toward the beams 168 of the interior tube 137 in a state of tension. The articulating region 135 of the tube assembly 131 curves until the bottoming segments 184 of the outer tube 132 bottom on each other. The articulating region 135 of the tube assembly 131 becomes rigid from the applied loading about the circumference holding the bottoming segments 184. Because there are no or relatively few and narrow gaps between bottoming segments 184 of the outer tube 132, relatively minimal tube curvature occurs and a substantially straight condition occurs. As the applied force is increased (e.g., the interior tube 137 is pushed further distal), the articulating region 135 becomes increasingly rigid and maintained in the substantially straight condition relative to the axis 145.

In another operational example, the interior tube 137 is pulled proximally with respect to the outer tube 132 to move the outer tube 132 distally with respect to the interior tube 137. The beams 178 of the outer tube 132 are put in tension and the beams 168 of the interior tube 137 are put in compression. The counterposing loading causes a curve in the articulating region 135 of the tube assembly 131 toward the beams 178 of the outer tube 132 in a state of tension. The articulating region 135 of the tube assembly 131 curves until the bottoming segments 174 of the inner tube 138 bottom on each other. The articulating region 135 of the tube assembly 131 becomes rigid from the applied loading about the circumference holding the bottoming segments 174. Because there are axial gaps between bottoming segments 174 of the inner tube 138, a substantially curved condition occurs. As the applied force is increased (e.g., the interior tube 137 is pulled further proximal), the articulating region 135 becomes increasingly rigid and maintained in the substantially curved condition relative to the axis 145.

The interior tube 137 is disposed within the outer tube 132 and comprises the lumen configured to receive the inner tube 138. In one example, the inner tube 138 is disposed within the interior tube 137 during actuation of the articulating region 135 such that the inner tube 138 conforms to the articulation provided by the articulating region 135. In another example, the inner tube 138 is inserted within the interior tube 137 subsequent to actuation of the articulating region 135. At least a portion of the inner tube 138 is flexible, enabling it to flex, deform, and/or conform to the articulating region 135. The inner tube 138 may comprise a non-metallic material such as extruded polymer, braided assembly, or composite depending on the application.

The inner tube 138 may be advanced may be advanced or retracted relative to the outer tube 132 (and the interior tube 137) during the surgical procedure from a retracted position in which a viewing assembly 143 to be described is proximal of a distal end 147 of the interior tube 137, to an advanced position in which the viewing assembly 143 is barely protruding of the distal end 147 of the interior tube 137, to even more advanced positions in which the viewing assembly 143 is more prominently protruding of the distal end 147 of the interior tube 137.

Figure 7:
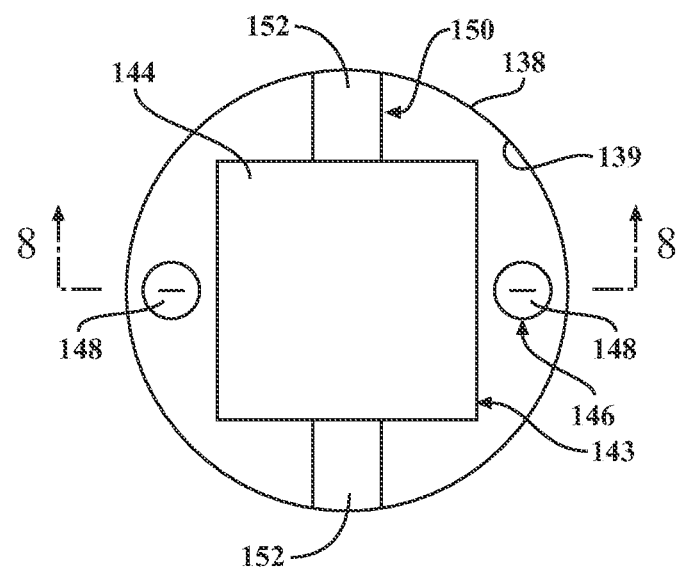
FIG. 7 is an elevational view of a distal end portion of the inner tube of FIG. 6.
Figure 8:
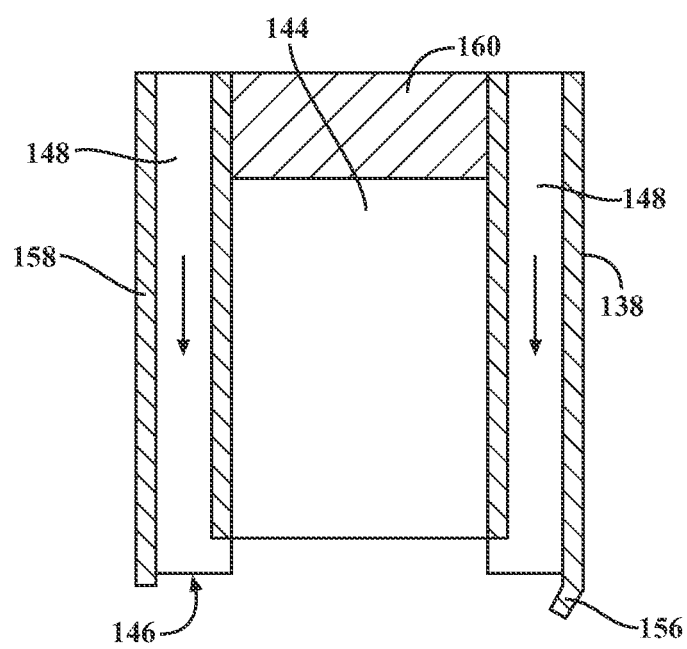
FIG. 8 is a sectional view taken along line 8-8 of FIG. 7.

The actuation assembly 141 is configured to steer the viewing assembly 143 when the distal end of the inner tube 138 is protruding from the distal end 147 of the interior tube 137. Referring to FIGS. 7 and 8, the actuation assembly 141 may comprise a steering assembly 150 with one or more steering control members 152 such as cables or stranded wire. The steering control members 32 are coupled to the distal end of the inner tube 138, such as by adhesive. A flex core 160 may be provided and coupled to the steering control members 152. The flex core 160 may be solid, hollow, or a combination thereof. Tensioning one steering control member 152 while releasing the other steering control member 152 causes the inner tube 138 to flex in the direction of the tensioned one of the steering control members 152, thereby steering the viewing assembly 143. In certain embodiments, the viewing assembly 143 may be rotatable relative to the articulating region 135 of the outer tube 132 due to the rotation of the inner tube 138 by the second handle 140.

The viewing assembly 143 is configured to visualize within a cavity or within the patient, such as during a surgical procedure. The viewing assembly 143 provides real time video to be presented to the user on a video monitor (not shown) for a primary view. In certain embodiments, the viewing assembly 143 provides a picture-in-picture video on the video monitor as a secondary view for an endoscope (not shown). In such an embodiment, the user maintains the "global view" with current visualization tools supplemented with perspective view deeper within the surgical site or cavity. The viewing assembly 143 comprises an image sensor 144 such as a camera, imaging element, video camera, or a camera chip, in communication with an image processing unit (not shown). The image sensor 144 and companion structures may be disposed within the inner tube 138. For example, the image sensor 144 is connected to the inner tube 138 by a joining means such as an adhesive. The inner tube 138 is configured to contain the image sensor 144 and leads.

The viewing assembly 143 may comprise an illumination assembly. In one embodiment, the illumination assembly comprises one or more illuminators or light fibers 148, such as light emitting diodes (LEDs). The light fibers 148 may be located on one side of an image sensor 144 to be described. The light fibers 148 are in communication with the illumination source 124 of the illumination system 114 (see FIG. 5). It should be appreciated that the light fibers 148 may be configured as a plastic optical fiber coupled to the light source disposed on or within at least one of the handles 134, 140. In one embodiment, the steering control members 152 comprise light fibers so that the steering control members 152 also transmit light while providing the steering function.

The tube assembly 131 may comprise an irrigation flow path 146. The single lumen 139 of the inner tube 138 may define the irrigation flow path 146 in communication with the fluid source of the irrigation system 112 (see FIG. 5). In certain embodiments, the irrigation flow path 146 is configured to irrigate the viewing assembly 143. The single lumen 139 may comprise a proximal region comprising the proximal end of the inner tube 138, and a distal region comprising the distal end 19 of the inner tube 18. The proximal region comprises a cross-sectional area greater than a cross-sectional area of the distal region to provide a nozzle-type effect for pressurized irrigation flow. In certain embodiments, the cross-sectional area of the proximal region is at least 50, 75, 100, 125, 150, 175, 200, 225, or 250%, larger than the distal region. The reduction in cross-sectional area within the single lumen 139 as the irrigation flow path 146 transitions to the distal region from the proximal region provides for the corresponding increase in pressure. A deflector 156 may be provided and coupled to the distal end 19 of the inner tube 18. The deflector 156 is configured to deflect the pressurized irrigation flow towards the viewing assembly 143 including the image sensor 144 and the light fibers 148. The deflected irrigation flow improves visibility of the viewing assembly 143 by clearing away debris disposed on or immediately ahead of the image sensor 144.

Referring to FIG. 8, the inner tube 138 is formed from a shroud or an extrusion 158 with the single lumen 139 defined by the extrusion 158. In certain embodiments, the extrusion 158 is the primary outer component of the inner tube 138 from the distal end towards the proximal end. It should be appreciated that the extrusion 158 may be comprised of the same material as the inner tube 138, or a different metallic and/or non-metallic material(s) depending on the requirements of the application.

In certain embodiments, the inner tube 138 may be configured to receive structures described herein, such as the imaging assembly, the illumination assembly, the irrigation assembly, and the like. In other embodiments, single lumen 139 defined by the extrusion 158 functions solely as a working channel capable of receiving any variety of working tools or devices such as graspers, cutter, power shavers, drills, radiofrequency devices, suction, etc. In still other embodiments, the surgical instrument 110 may provide one or more of these working tools as part of the inner tube 138.

Methods of manipulating the instrument 10, 110 are also contemplated. The instrument comprises the tube assembly 11, 131 adapted to be grasped by a single hand of a user and comprising the outer tube 12, 132 having the articulating region 135, the inner tube having the single lumen 25, 139 and the articulating region 135, the first handle 14, 134 coupled to the outer tube 12, 132, and the second handle 20, 140 coupled to the inner tube 18, 138. It should be noted that the articulating region 135 of the outer tube 12, 132 may be used interchangeably with the curved region 17 of the outer tube 12, 132 when the articulating region 135 is articulated and assumes a curved shape. The instrument 10, 110 further comprises the viewing assembly 23, 143 disposed within the single lumen 25, 139 and coupled to the inner tube 18, 138, and the actuation assembly 21, 141 coupled to the second handle 20, 140 and the inner tube 18, 138. With the first handle 14, 134 grasped by the user in the single head, the articulating region 135 of the outer tube 12, 132 is positioned tube through an orifice and within a cavity, such as a nasal cavity. The inner tube 18, 138 is positioned within a lumen of the outer tube 12, 132. With the second handle 20, 140 grasped by the single hand, at least a portion of the inner tube 18, 138 is positioned beyond a distal end of the outer tube 12, 132 and into the cavity. With the actuation assembly 21, 141 actuated by the single hand, the viewing assembly 23, 143 is steered within the cavity in response to articulation of the articulating region 135. Within the cavity is viewed with the viewing assembly 23, 143. The step of actuating the actuation assembly 21, 141 to articulate the articulating region 135 of the outer tube 12, 132 and the inner tube 18, 138 is disclosed in International Patent Application No. PCT/US2016/019880.

The advantages of the present invention are several. The surgical instrument with the steerable camera within a single lumen provides a small profile to facilitate reduced incision size, improve access and visibility, and enhance surgical outcomes with quicker recovery. The outer tube with the curved region (e.g., malleable, rigid, or comprising the articulating region), provides improved placement of the camera in remote locations within the patient. The positioning and actuating to selectively position and reposition the camera may be achieved with a single hand of the user, thereby freeing the other hand of the user to perform other critical tasks. The inner tube is designed to provide pressurized irrigation flow to remove debris from the viewing assembly and the illumination assembly. The deflector directs the pressurized irrigation flow in a desirable manner.

The present invention has been described in an illustrative manner. It is to be understood that the terminology, which has been used, is intended to be in the nature of words of description rather than of limitation. Many modifications and variations of the present invention are possible in light of the above teachings. Therefore, the present invention may be practiced other than as specifically described.

What is claimed is:

1. A surgical instrument for use on a patient, said surgical instrument comprising:
   an outer tube comprising a distal end, a proximal end opposite said distal end, a lumen extending between said proximal and distal ends, and an articulating region intermediate said proximal and distal ends;
   an interior tube disposed within said lumen of said outer tube and comprising a proximal end, a distal end opposite said proximal end, a lumen extending between said proximal and distal ends, and an articulating region intermediate said proximal and distal ends, wherein said outer tube and said interior tube are fixedly coupled to one another distal to said articulating regions and axially movable relative to one another proximal said articulating regions such that axial movement of said interior tube relative to said outer tube articulates said articulating regions of said outer tube and said interior tube between a substantially straight condition and a substantially curved condition;
   an inner tube movably disposed within said lumen of said interior tube and comprising a distal end, a proximal end opposite said distal end with said inner tube configured to conform to said articulating regions of said outer tube and said interior tube in said substantially straight and curved conditions;
   a first handle coupled to said outer tube;
   a second handle coupled to said inner tube with said first and second handles axially movable relative to one another so as to move said inner tube within said outer and interior tubes;
   a viewing assembly coupled to said inner tube; and
   an actuation assembly coupled to said second handle and configured to articulate said inner tube and steer said viewing assembly when said distal end of said inner tube is exposed beyond said distal ends of said outer and interior tubes,
   wherein said first handle, said second handle, and said actuation assembly are complementarily arranged such that said outer tube is positionable, said articulating regions are articulable, and said viewing assembly is steerable by a user grasping said surgical instrument with a single hand.

2. The surgical instrument of claim 1, wherein said articulating regions define a single plane in said substantially curved condition, and wherein said inner tube is configured to be articulated in said single plane in one of a same direction and opposite direction to provide compound articulation when said articulating regions are in said substantially curved condition.

3. The surgical instrument of claim 1, wherein each of said articulating regions further comprise apertures defining bottoming segments with an adjacent two of said bottom segments of one of said articulating regions configured to abut one another and provide rigidity to said articulating regions in said substantially straight condition and said substantially curved condition.

4. The surgical instrument of claim 3, further comprising a rotatable collar rotatably coupled to said first handle and configured to receive an input from the user to lock and maintain the rigidity of said articulating regions in said substantially curved condition or said substantially straight condition.

5. The surgical instrument of claim 4, wherein said rotatable collar is complementarily arranged with said first handle, said second handle, and said actuation assembly are complementarily arranged such that said articulating regions are lockable by the user grasping said surgical instrument with the single hand.

6. The surgical instrument of claim 1, wherein said inner tube defines a single lumen defining an irrigation flow path in communication with a fluid source with said irrigation flow path configured to direct pressurized irrigation fluid from the fluid source to irrigate said viewing assembly.

7. The surgical instrument of claim 6, wherein said single lumen comprises a proximal region comprising said proximal end of said inner tube, and a distal region comprising said distal end of said inner tube, wherein said proximal region has a cross-sectional area greater than a cross-sectional area of said distal region to provide a nozzle-type effect for the pressurized irrigation fluid.

8. The surgical instrument of claim 6, further comprising a deflector coupled to said distal end of said inner tube and configured to deflect the pressurized irrigation fluid towards said viewing assembly.

9. The surgical instrument of claim 1, further comprising an illumination assembly comprising one or more illuminators coupled to said inner tube near said distal end of said inner tube and configured to illuminate said viewing assembly.

10. A method of manipulating an instrument with a single hand through a nasal passage of a patient with the instrument including an outer tube having an articulating region, an interior tube disposed within a lumen of the outer tube and fixed to the outer tube distal to articulating regions, an inner tube, a viewing assembly coupled to the inner tube, a first handle coupled to the outer tube, a second handle, and an actuation assembly coupled to the second handle, said method comprising the steps of:

positioning with the first handle grasped by the single hand the outer tube within the nasal passage;

axially moving the second handle grasped by the single hand relative to the first handle to expose a distal portion of the inner tube beyond a distal end of the outer tube positioned within the nasal passage;

axially moving the interior tube relative to the outer tube, wherein the interior tube and the outer tube being fixed distal to the articulation regions causes the articulation regions to articulate to a substantially curved condition with the inner tube conforming to the articulating regions in the substantially curved condition;

actuating the actuation assembly with the single hand to articulate the inner tube and steer the viewing assembly within the patient with the articulating regions in the substantially curved condition; and viewing within the patient with the viewing assembly.

11. The method of claim 10, further comprising the step of inserting the inner tube within the interior tube prior to the step of positioning the outer tube within the nasal passage, wherein the inner tube conforms to the articulating regions as the articulating regions articulate to the substantially curved condition.

12. The method of claim 10, further comprising the step of inserting the inner tube within the interior tube after the step of positioning the outer tube within the nasal passage and before the step of axially moving the interior tube relative to the outer tube, wherein the inner tube conforms to the articulating regions as the articulating regions articulate to the substantially curved condition.

13. The method of claim 10, further comprising the step of inserting the inner tube within the interior tube after the step of positioning the outer tube within the nasal passage and after the step of axially moving the interior tube relative to the outer tube, wherein the inner tube conforms to the articulating regions in the substantially curved condition as the inner tube is inserted within the interior tube.

14. The method of claim 10, wherein the step of axially moving the second handle relative to the first handle exposes the distal portion of the inner tube beyond the distal end of the outer tube by a first distance, and the actuation of the actuation assembly with the distal portion exposed by the first distance provides a first radius of curvature of the inner tube, said method further comprising the step of axially moving the second handle relative to the first handle to expose the distal portion of the inner tube beyond the distal end of the outer tube by a second distance greater than the first distance, and actuating the actuation assembly with the distal portion of the inner tube exposed by the second distance providing a second radius of curvature greater than the first radius of curvature.

\* \* \* \* \*